United States Patent
Kiedrowski

(10) Patent No.: US 10,642,022 B2
(45) Date of Patent: May 5, 2020

(54) EYEPIECE DEVICE FOR A SURGICAL INSTRUMENT

(71) Applicant: OLYMPUS WINTER & IBE GMBH, Hamburg (DE)

(72) Inventor: Gregor Kiedrowski, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 275 days.

(21) Appl. No.: 15/681,567

(22) Filed: Aug. 21, 2017

(65) Prior Publication Data

US 2017/0371146 A1 Dec. 28, 2017

Related U.S. Application Data

(63) Continuation of application No. PCT/EP2016/052114, filed on Feb. 2, 2016.

(30) Foreign Application Priority Data

Feb. 25, 2015 (DE) .......................... 10 2015 203 351

(51) Int. Cl.
  *A61B 1/00* (2006.01)
  *G02B 25/00* (2006.01)
  (Continued)

(52) U.S. Cl.
  CPC .......... *G02B 25/001* (2013.01); *A61B 1/0011* (2013.01); *A61B 1/00195* (2013.01);
  (Continued)

(58) Field of Classification Search
  CPC . A61B 1/00195; A61B 1/00006; A61B 1/051; A61B 1/0684; A61B 2090/0813;
  (Continued)

(56) References Cited

U.S. PATENT DOCUMENTS 4,611,888 A * 9/1986 Prenovitz ............... A61B 1/042
  348/75
5,307,804 A  5/1994 Bonnet
  (Continued)

FOREIGN PATENT DOCUMENTS

CN  102004309 A  4/2011
DE  102011007875 A1  7/2012
  (Continued)

OTHER PUBLICATIONS

International Search Report dated Apr. 6, 2016 issued in PCT/EP2016/052114.
(Continued)

*Primary Examiner* — Timothy J Neal
(74) *Attorney, Agent, or Firm* — Scully, Scott, Murphy & Presser, P.C.

(57) ABSTRACT

An eyepiece device for a surgical instrument, the eyepiece device including: an eyepiece frame; and at least one optical unit accommodated in the eyepiece frame, wherein the at least one optical unit comprises at least one first optical element and a second optical element connected with the at least one first optical element, wherein the second optical element is formed from a second material with abnormal dispersion and the first and the second optical elements together correct chromatic aberration; wherein the eyepiece frame comprises an expansion chamber for at least the second optical element, the expansion chamber forming an installation space for at least the second optical element in a radial direction.

12 Claims, 3 Drawing Sheets

(51) Int. Cl.
  *G02B 27/00* (2006.01)
  *G02B 23/24* (2006.01)
  *G02B 7/02* (2006.01)
  *A61B 90/00* (2016.01)
  *A61B 1/05* (2006.01)
  *A61B 1/06* (2006.01)

(52) U.S. Cl.
  CPC ............. *G02B 7/025* (2013.01); *G02B 7/028* (2013.01); *G02B 23/2453* (2013.01); *G02B 27/0025* (2013.01); *A61B 1/00006* (2013.01); *A61B 1/051* (2013.01); *A61B 1/0684* (2013.01); *A61B 2090/0813* (2016.02)

(58) Field of Classification Search
  CPC ...... G02B 25/001; G02B 7/025; G02B 7/028; G02B 27/0025
  See application file for complete search history.

(56) References Cited

U.S. PATENT DOCUMENTS

| | | | |
|---|---|---|---|
| 5,569,163 A | 10/1996 | Francis et al. | |
| 6,181,481 B1* | 1/2001 | Yamamoto | G02B 9/12 359/558 |
| 6,282,030 B1 | 8/2001 | Hall | |
| 6,695,775 B2 | 2/2004 | Watanabe et al. | |
| 2001/0036019 A1 | 11/2001 | Fukumoto | |
| 2005/0228229 A1* | 10/2005 | Harris | G02B 21/0028 600/168 |
| 2006/0187323 A1* | 8/2006 | Kobayashi | G02B 15/177 348/240.99 |
| 2010/0265355 A1* | 10/2010 | Sato | G02B 13/0045 348/222.1 |
| 2013/0063812 A1 | 3/2013 | Matsumoto | |
| 2014/0313578 A1 | 10/2014 | Schouwink et al. | |

FOREIGN PATENT DOCUMENTS

| | | |
|---|---|---|
| DE | 102012200146 A1 | 7/2013 |
| EP | 0501088 A1 | 9/1992 |
| JP | S58-168708 U | 11/1983 |
| JP | H09-080269 A | 3/1997 |
| JP | H09-274146 A | 10/1997 |
| JP | 2001-305438 A | 10/2001 |
| JP | 2002-365560 A | 12/2002 |
| JP | 2009-251302 A | 10/2009 |
| WO | 2011/148579 A1 | 12/2011 |
| WO | WO-2013102476 A1 * | 7/2013 ......... G02B 27/0025 |

OTHER PUBLICATIONS

Japanese Office Action dated Nov. 27, 2018 in Japanese Patent Application No. 2017-545368.
Japanese Office Action dated Aug. 6, 2019 in Japanese Patent Application No. 2017-545368.

* cited by examiner

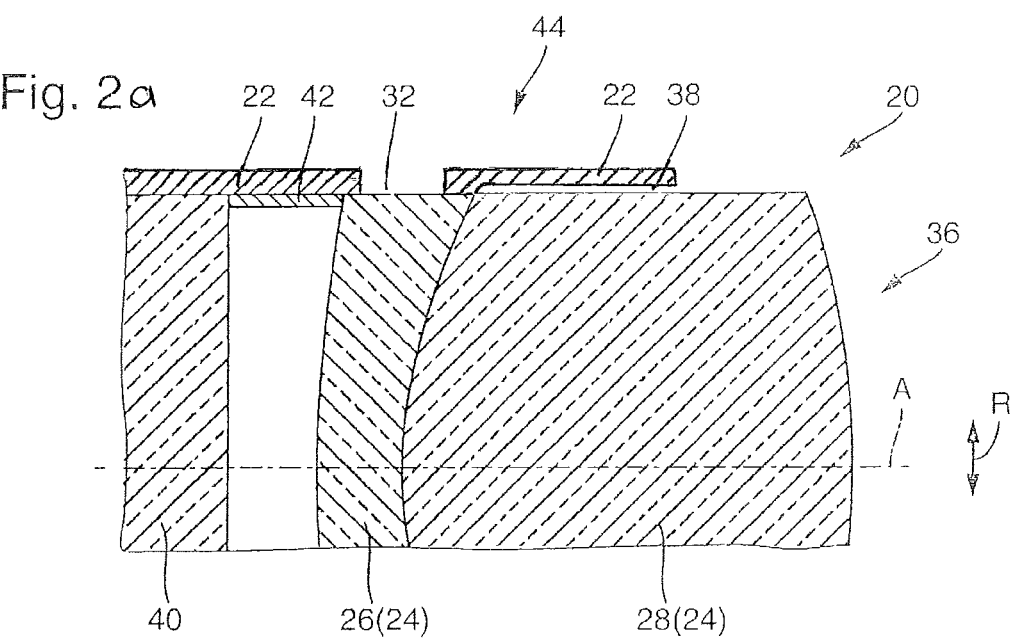
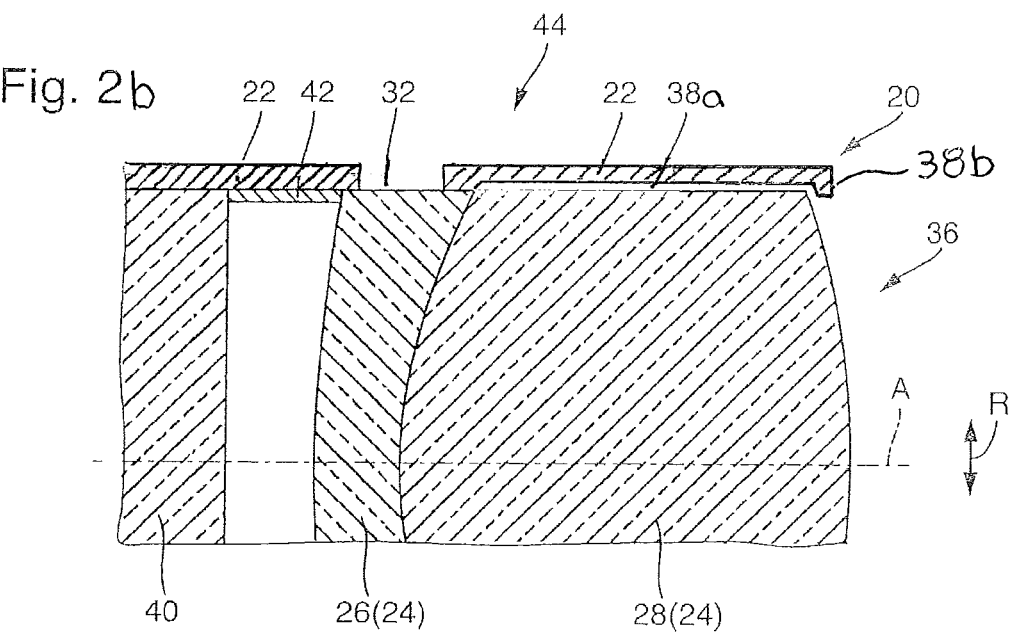

EYEPIECE DEVICE FOR A SURGICAL INSTRUMENT

CROSS-REFERENCE TO RELATED APPLICATION

The present application is a continuation of PCT/EP2016/052114 filed on Feb. 2, 2016, which is based upon and claims the benefit to DE 10 2015 203 351.1 filed on Feb. 25, 2015, the entire contents of each of which are incorporated herein by reference.

BACKGROUND

Field

The present application relates to an eyepiece device for a surgical instrument, such as an endoscope, wherein the eyepiece device comprises an eyepiece frame and at least one optical unit which is accommodated in the eyepiece frame, wherein the optical unit comprises at least one first optical element and a second optical element connected therewith, wherein the second optical element is manufactured from a second material with abnormal dispersion and the first and the second optical elements together form an optical unit which is corrected in respect of chromatic aberration. The present application also relates to an eyepiece comprising such an eyepiece device and a surgical instrument having such an eyepiece.

Prior Art

Surgical instruments, for example endoscopes, for minimally invasive surgery on the human or animal body are generally known. In the case of an endoscope, an operation or examination field inside the body is observed with the aid of optics at a distal tip of an endoscope shaft. To this end, multiple optical assemblies are arranged in the endoscope shaft, with which optical assemblies light is guided from a body cavity to a proximal end of the endoscope.

An eyepiece cap having an eyepiece is frequently located at the proximal end of the endoscope, for example on a handle which is used to operate the endoscope. The light entering at the distal tip of the endoscope exits the endoscope again at this optical mounting. The eyepiece is partially used to directly observe the operation field with the naked eye. In many cases it is, however, envisaged that a camera head is connected to the eyepiece so that the operation field is observed on a monitor, or the captured image data can be made available for image processing. Such an endoscope emerges, for example, from EP 0 501 088 AI.

Imaging errors, for example chromatic aberration, inevitably occur in optical imaging systems. Said chromatic aberration is generated by the dispersion of optical glasses, as light of differing wavelengths is deflected to varying degrees. The refractive index of a glass is not a constant function, but is dependent on the wavelength. The chromatic aberrations are reduced by using lenses with different dispersion. In the case of an achromat, the axial chromatic aberration is therefore corrected for two wavelengths. In the case of an apochromat, the axial chromatic aberration is corrected for three wavelengths.

In the case of an optical unit which is configured as an achromat or as an apochromat, glasses with a chromal or particularly low dispersion are used. These glasses are referred to as ED glass for "extra low dispersion glass", as SLD glass for "special low dispersion glass", as ELD glass for "extraordinary low dispersion glass" or as UL glass for "ultra low dispersion glass". Within the context of the present specification, such glasses are to be collectively referred to generally as "ED glass".

Surgical instruments, for example endoscopes, are sterilized following use. To this end, they are treated with a rinsing and cleaning solution and are frequently subjected to heat treatment in an autoclave during a disinfection step.

SUMMARY

It is an object to indicate an eyepiece device for a surgical instrument, an eyepiece comprising an eyepiece device and a surgical instrument having an eyepiece, wherein a further objective is to improve a temperature resistance of the eyepiece device, the eyepiece and the surgical instrument, especially at the temperatures that typically occur during autoclaving.

Such object can be solved by an eyepiece device for a surgical instrument, such as an endoscope, wherein the eyepiece device comprises an eyepiece frame and at least one optical unit which is accommodated in the eyepiece frame, wherein the optical unit comprises at least one first optical element and a second optical element connected therewith, wherein the second optical element is manufactured from a second material with abnormal dispersion and the first and the second optical elements together form an optical unit which is corrected in respect of chromatic aberration, wherein the eyepiece device is developed by virtue of the eyepiece frame comprising an expansion chamber for the second optical element, wherein the expansion chamber extends an installation space provided for the optical unit in a radial direction.

The optical elements of an optical unit, for example of an achromat or an apochromat which is corrected in respect of chromatic aberration, can have, in addition to different dispersion properties, different thermal expansion coefficients. The materials used to correct chromatic aberrations, for example glasses with abnormal dispersion, expand to a greater extent on heating than glasses with normal dispersion. In addition, materials with abnormal dispersion are frequently significantly more brittle than conventional glasses.

While differences in the thermal expansion coefficients are not critical in many applications, for example in the case of objectives for photography, they can have a significant importance when using optical units in a surgical instrument. During the sterilization of the surgical instrument, the latter is exposed to temperatures of more than 100° C. in an autoclave. At this temperature which is significantly higher than room temperature, an appreciably different expansion of the optical elements of the optical unit occurs. The optical element having abnormal dispersion shows a greater thermal expansion than the optical element with normal dispersion.

In order to prevent damage to the optical unit, such as to the second optical element, the eyepiece frame can comprise an expansion chamber for the second optical element, wherein the expansion chamber extends an installation space provided for the optical unit in a radial direction. The first optical element can be in addition mechanically accommodated in the eyepiece frame. In other words, there can be at least one mechanical connection element between the eyepiece frame and the first optical element for accommodating the optical unit in the eyepiece frame.

The forces occurring as a consequence of the heat treatment and the resulting material expansion therefore occur between the first optical element and the eyepiece frame.

The second optical element, which is frequently manufactured from a mechanically more brittle material, is not exposed to any mechanical load or is exposed to a significantly lower mechanical load. As a result, the temperature resistance of the eyepiece device is significantly improved, especially with regard to the temperatures occurring during an autoclave treatment.

A single or multiple mechanical connection elements can be provided between the eyepiece frame and the first optical element. In other words, no direct mechanical connection is necessary between the second optical element and the eyepiece frame.

In addition, a mechanical contact can be avoided between the second optical element and the eyepiece frame due to the expansion chamber which can extend the installation space provided for the optical unit in a radial direction. Said second optical element expands into the existing expansion chamber during the temperature treatment. This measure improves the temperature resistance of the eyepiece device.

The expansion chamber can increase a diameter of the eyepiece frame in the region of the second optical element with respect to a diameter of the eyepiece frame in the region of the first optical element, wherein as the expansion chamber, such as a groove or a recess, is recessed into the eyepiece frame, wherein the groove or the recess can be closed in a circumferential direction of the second element. The groove or recess can, for example, have the form of a hollow cylinder, with the installation space occupied by the second optical element abutting on the inside thereof and the inside of the eyepiece frame abutting on the outside thereof.

A region of an optical element can be a cylindrical region, in which the optical element extends in the radial direction and in the longitudinal direction, i.e. along the optical axis. In other words, the diameter of the eyepiece frame can be extended along the entire length of the second optical element with respect to the adjoining regions. This can avoid a mechanical contact between the second optical element and an inside of the eyepiece frame.

A mechanical contact between the second optical element and an inside of the eyepiece frame can also be avoided in that the second optical element can have a smaller diameter than the first optical element, such as where the optical elements are lenses.

The mechanical connection element, with which the first optical element is held in the eyepiece frame, can be a bonding bore filled with adhesive. Furthermore, multiple bonding bores filled with adhesive can be provided in the eyepiece frame, by means of which the first optical element is held along its circumference in the eyepiece frame.

The first material can have a first thermal expansion coefficient and the second material having a second thermal expansion coefficient, wherein the second thermal expansion coefficient is greater, such as at least by a factor of two, than the first thermal expansion coefficient.

The first optical element can be manufactured from a first material with a first Abbe number and the second optical element can be manufactured from a second material with a second Abbe number, wherein the second Abbe number is greater than the first Abbe number.

Within the context of the present specification the Abbe number V is calculated from the refractive index n of the material used, which is dependent on the wavelength, as follows:

$$V = \frac{n_e - 1}{n'_F - n'_C}$$

The Abbe number is a measure of the dispersion of the material, wherein a low Abbe number represents a high dispersion and a high Abbe number represents a low dispersion. In the aforementioned formula, the indices e, F' and C' represent the Fraunhofer lines e (mercury, wavelength 546.074 nm), F' (cadmium at 479.9915 nm) and C' (cadmium at 643.8469 nm).

The second glass can be an ED glass. Within the context of the present specification and claims, ED glass, SLD glass, ELD glass and UL glass are collectively referred to as ED glass. The ED glass can have an Abbe number greater than 75. The Abbe number of the second material is, for example, between 77 and 95, such as between 77 and 80. The glass used as the second material can be a fluoride glass, for example a calcium fluoride glass or a fluoride phosphate glass. Such material parameters can be advantageous for the production of the optical elements of the optical unit which has been corrected in respect of chromatic aberration.

If the optical elements are lenses, the optical unit can be an achromat or an apochromat. The second optical element can be an eyepiece lens. In other words, the second optical element can be an external lens of the eyepiece device. The latter can also be used in a surgical instrument.

Such object can also be solved by an eyepiece comprising an eyepiece device according to one or more of the indicated embodiments, wherein the optical unit comprising an eyepiece lens of the eyepiece. Such object can also be achieved by a surgical instrument, such as an endoscope, comprising such an eyepiece.

The same or similar advantages as those already mentioned with respect to the eyepiece device apply to the eyepiece or the surgical instrument having such an eyepiece. For this reason, these are not set out again.

The first and the second optical elements, which can be lenses, can be cemented or glued to one another. The lenses are, for example, biconvex, biconcave or concave-convex lenses. The surfaces facing each other of the first and the second optical elements can be configured in a form which complements one another. In addition to glued or cemented lens systems, systems having an air gap can also be used. Such air gap can be located between the first and second optical elements.

The optical elements can be arranged together with their eyepiece frame in a proximal region of an endoscope. The endoscope can have a rigid endoscope shaft.

BRIEF DESCRIPTION OF THE DRAWINGS

Further features will become evident from the description of embodiments together with the claims and the appended drawings. Embodiments can fulfill individual features or a combination of several features.

The embodiments will be described below without limiting the general concept of the invention by means of exemplary embodiments with reference to the drawings, wherein reference is expressly made to the drawings regarding all of the details which are not explained in greater detail in the text, wherein:

FIGS. 2a-2c illustrate first to third variations, respectively, of schematically simplified longitudinal sectional views through an eyepiece device.

The same or similar elements and/or parts are, in each case, provided with the same reference numerals in the drawings so that these will not be presented again.

DETAILED DESCRIPTION

Figure 1:
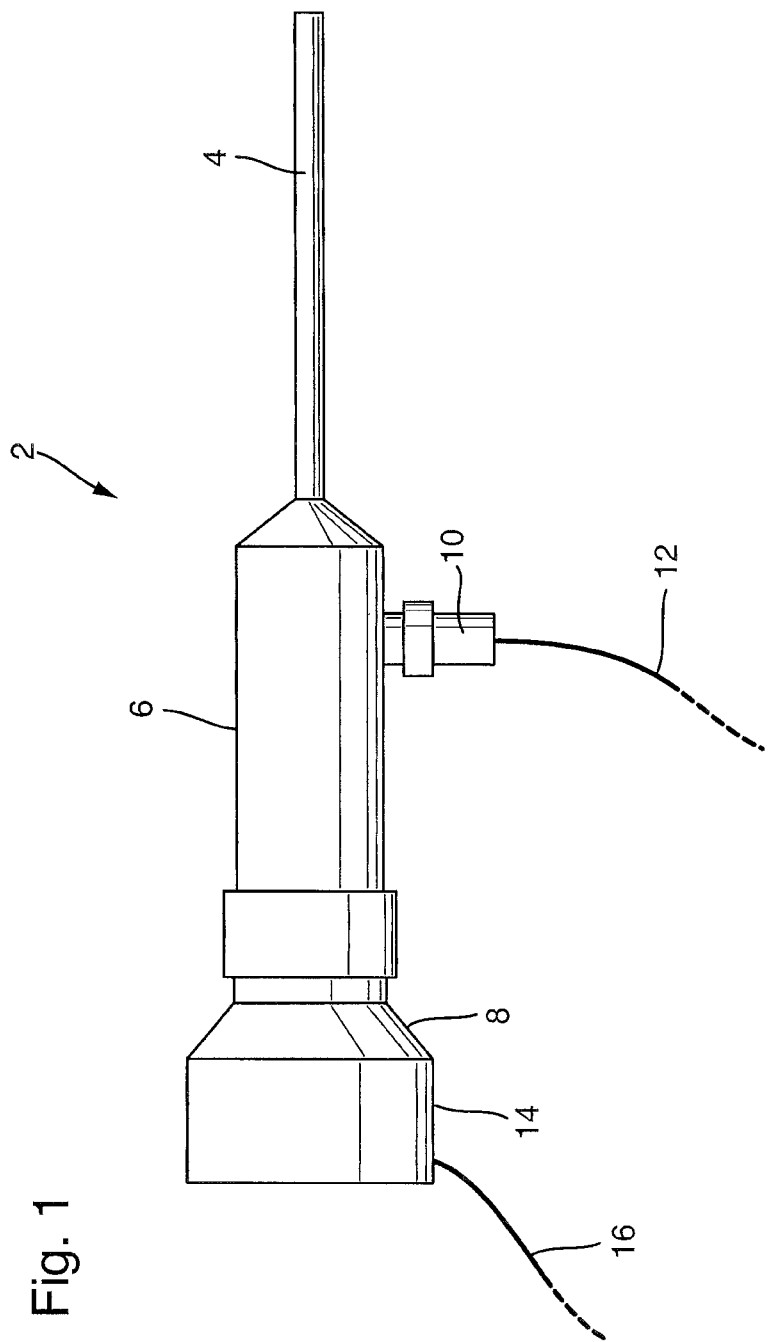
FIG. 1 illustrates a schematic and simplified side view of a surgical instrument, by way of an exemplary endoscope.

FIG. 1 shows a schematic and simplified side view of a surgical instrument 2, by way of example an endoscope. At its distal end, the endoscope comprises a tubular shaft 4 having optics which make it possible to observe an operation and examination field which is located distally before a free end of the shaft 4. The shaft 4 opens out into a housing 6 which has an eyepiece cap 8 at the proximal end. The housing 6 is used to handle the surgical instrument 2. Located laterally on the housing 6 is a light source 10, for example a LED light source. This is connected via a connecting cable 12 to a suitable power supply 12.

A camera head 14, which is shown schematically, having an eyepiece adapter (not shown) is arranged on the eyepiece cap 8. The camera head 14 captures the light exiting from the eyepiece (not shown) of the surgical instrument 2 with suitable optics and images the light on an optical area sensor, for example a CCD or CMOS chip. The camera head 14 is supplied with electricity by means of a connection 16. It is also possible to transmit image signals from the area sensor of the camera head 14 to an external evaluation unit via the connection 16 and to transfer control signals to the camera head 14.

FIG. 2a shows a schematic and simplified longitudinal section of a part of an eyepiece device 20 as provided in the region of the eyepiece cap 8 at the proximal end of the surgical instrument 8, for example an endoscope (see FIG. 1).

The eyepiece device 20 comprises an eyepiece frame 22 in which an optical unit 24 is accommodated. The optical unit comprises, in turn, a first optical element 26 and a second optical element 28. In the exemplary embodiment shown, the optical elements 26, 28 are by way of example lenses. The two optical elements 26, 28 together form the optical unit 24 which is corrected in respect of chromatic aberration. An achromat is also shown by way of example. According to other exemplary embodiments, the optical unit 24 comprises additional optical elements so that an apochromat is provided for example.

The first optical element 26 is manufactured from a first material, for example a first glass or a first type of glass. The second optical element 28 is manufactured from a second material, for example from a second glass or a second type of glass. The second material, i.e. for example the second type of glass, is a material with abnormal dispersion. This is, for example, an ED glass. Within the context of the present specification and claims, ED glass, SLD glass, ELD glass and UL glass are collectively referred to as ED glass. An Abbe number of the glass used for producing the second optical element 28 can be greater than 75. For example, a fluoride glass can be used to produce the second optical element 28.

The first material used for producing the first optical element 26, for example the first type of glass, has a first Abbe number, while the second material, from which the second optical element 28 is manufactured, has a second Abbe number. The second Abbe number can be greater than the first Abbe number.

The two optical elements 26, 28, for example a concave-convex lens used as a first optical element 26 and a biconvex lens used as a second optical element 28 are preferably glued or cemented to one another. The two optical elements 26, 28 are connected to one another in this way. It is also envisaged that an air gap is provided between the surfaces facing one another of the first and second optical elements 26, 28, which optical elements are cemented or glued to one another in the exemplary embodiment shown. In such an embodiment, the two optical elements 26, 28 are connected to one another in another way, for example by an enveloping tube.

Figure 3:
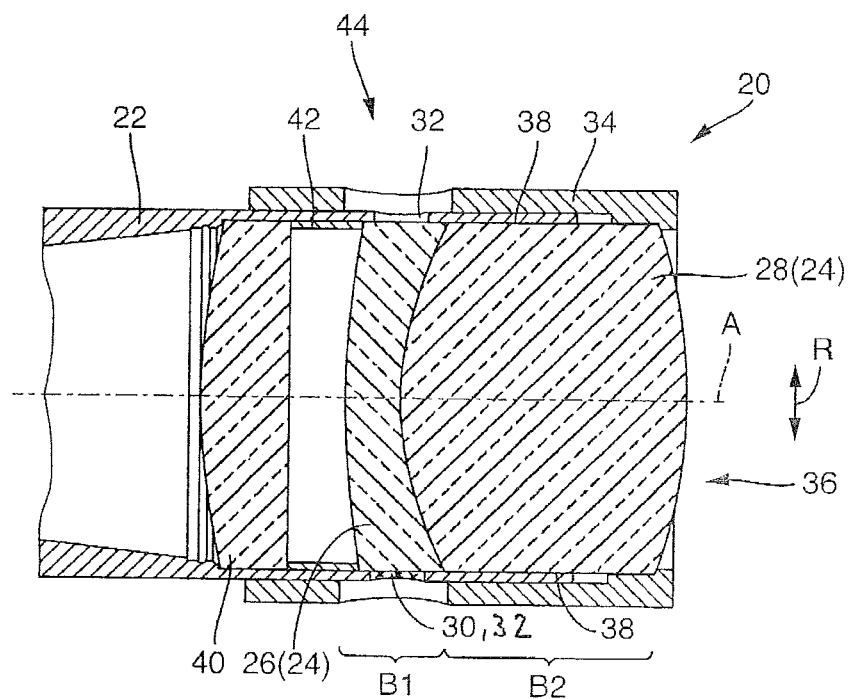
FIG. 3 illustrates a further schematically simplified longitudinal section.

The optical unit is inserted into the eyepiece frame 22 from right to left. Since only a relatively short guide length exists, a mounting aid 34 is provided. FIG. 3 shows a detailed view of the eyepiece device 20 and a simplified and a schematic longitudinal section view with an attached mounting aid 34.

The optical unit 24 is accommodated in the eyepiece frame 22 by means of at least one mechanical connection element 30. By way of example, this mechanical connection element 30 is a bonding bore 32 filled with adhesive. The mechanical connection element 32 only acts upon the first optical element 26. In other words, the second optical element 28 is therefore not connected directly to the eyepiece frame 22, but simply indirectly by means of the first optical element 26.

In order to illustrate this, FIG. 3 shows a bonding bore 32 which is not filled with adhesive on the side of the eyepiece device 20 which is shown at the top. The bonding bore 32 shown on the lower side of the eyepiece device 20 is, on the other hand, filled with an adhesive that is shown in cross-hatching. In the hardened state, it forms the mechanical connection element. The bonding bore 32 extends through the eyepiece frame 22. It extends at least approximately in a radial direction R vertical to an optical axis A of the optical unit 24 through the wall of the eyepiece frame 20.

The mounting aid 34 shown, which encloses the eyepiece frame 22 in regions on its outside, is equipped with a free hole which is arranged above the bonding bore 32 so that an adhesive nozzle can be taken directly up to the bonding bore 32. The mounting aid 34 extends on an eyepiece outlet side 36 across the second optical element 28. The optical unit 24 is thus held during mounting until the adhesive has hardened, both in a longitudinal direction, i.e. parallel to the optical axis A, and in the radial direction R.

The eyepiece device 20 is observed from the eyepiece outlet side 36. If the eyepiece device is in an endoscope, an examination field at the distal end of the endoscope shaft 4 is observed from this direction (FIG. 1). In other words, the rays of light entering the shaft 4 of the surgical instrument 2 distally on the eyepiece outlet side 36 exit again from the surgical instrument 2 and, for example, hit a flat image sensor of the camera head 14.

The optical unit 24 which has been corrected in respect of chromatic aberration comprises, as already indicated, a first optical element 26 made of a first material and a second optical element 28 made of a second material. The first material has a first thermal expansion coefficient and the second material has a second thermal expansion coefficient. If the eyepiece device 20 which is present, for example, in a surgical instrument 2 is heated, e.g. because the surgical instrument 2 is sterilized in an autoclave, the first optical element 26 and the second optical element 28 will expand to varying degrees. This thermal expansion which is determined by the first or second expansion coefficients sometimes differs greatly, as the second thermal expansion coefficient of the second optical element 28 is, for example, greater by a factor of two or more than the first thermal expansion coefficient of the first optical element 26. In order to prevent damage to the second optical element 28 due to its thermal expansion, in particular in the radial direction R, i.e. perpendicular to the optical axis A, an expansion chamber 38 (visible in FIG. 2) is provided.

The expansion chamber 38 for the second optical element 28 extends the installation space provided for the optical unit 24 in the eyepiece frame 22 in the radial direction R. Due to the virtually true-to-scale representation in FIGS. 2 and 3, the expansion chamber 38 is very small in the radial direction R and below the line width used for the representation.

The expansion chamber 38 extends a diameter of the eyepiece frame 22 in a second region B2 of the second optical element 28 with respect to a diameter of the eyepiece frame 22 in a first region B1 of the first optical element 26. As shown in FIG. 2b, the expansion chamber 38 has, for example, the form of a groove or recess 38a recessed into the eyepiece frame 22. The groove or recess can be closed in the circumferential direction of the second optical element 28 by tab 38b.

The regions B1, B2 of the first or second optical elements 26, 28 can be those regions at which the corresponding optical element 26, 28 touches an inside of the eyepiece frame 22 with its outside edge (in the case of the first optical element 26) or faces this (in the case of the second optical element 28). The expansion chamber 38 has the form of a hollow cylinder 38, for example. An outside or casing surface of the second optical element 28 adjoins an inside of this hollow cylinder. An inside or inner casing surface of the eyepiece frame 22 adjoins an outer side or outer casing surface of this hollow cylinder. The expansion chamber 38 or the groove or recess are closed in particular in the circumferential direction of the second optical element 28 so that the second optical element can expand uniformly in all radial directions R.

Figure 2C:
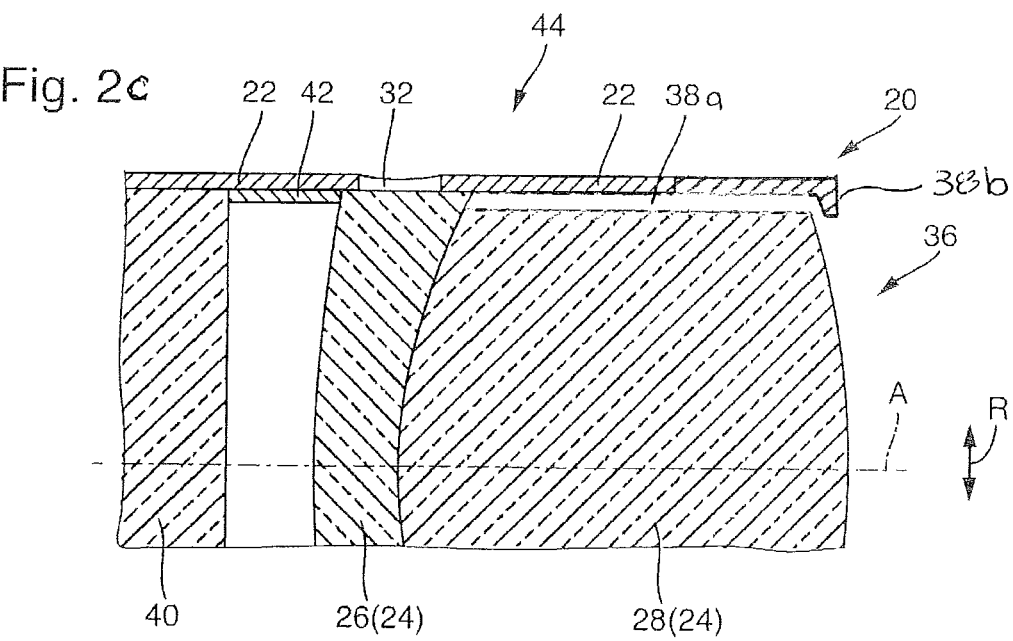

Alternatively or additionally to a groove or recess recessed into the eyepiece frame 22, as shown in FIG. 2c, the second optical element 28 can have a smaller diameter than the first optical element 26. This diameter is also observed in the radial direction R. In this way, an expansion chamber 38 is also created along the outer casing surface of the second optical element 28.

There is also another lens 40 (see FIG. 3), which is located at a distance from the optical unit 24 by means of a spacer ring 42 and which is also held in this way in the eyepiece frame 22. Together with the additional lens 40, the optical unit 24 forms an eyepiece 44 as it is comprised by the surgical instrument 2 (FIG. 1) in its eyepiece cap 8 for example. In this case, the second optical element 28 which is manufactured from a material with abnormal dispersion, for example an ED glass, is the eyepiece lens of this eyepiece 44.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Surgical instrument
4 Shaft
6 Housing
8 Eyepiece cap
10 Light source
12 Connecting cable
14 Camera head
16 Connection
20 Eyepiece device
22 Eyepiece frame
24 Optical unit
26 First optical element
28 Second optical element
30 Mechanical connection element
32 Bonding bore
34 Mounting aid
36 Eyepiece outlet side
38 Expansion chamber
40 Additional lens
42 Spacer ring
44 Eyepiece
A Optical axis
R Radial direction
B1 Region of the first optical element
B2 Region of the second optical element

What is claimed is:

1. An eyepiece device for a surgical instrument, the eyepiece device comprising:
an eyepiece frame; and
at least one optical unit accommodated in the eyepiece frame, wherein the at least one optical unit comprises at least one first optical element and a second optical element connected with the at least one first optical element, wherein the second optical element is formed from a second material with anomalous dispersion and the first and the second optical elements together correct chromatic aberration;
wherein the eyepiece frame comprises an expansion chamber for at least the second optical element, the expansion chamber forming an installation space for at least the second optical element in a radial direction;
the expansion chamber increases an inner diameter of the eyepiece frame in at least a portion of a region of the second optical element with respect to a diameter of the eyepiece frame in a region of the first optical element;
the expansion chamber comprises a groove or a recess recessed into the eyepiece frame; and
the groove or the recess is closed in a circumferential direction of the second optical element.

2. The eyepiece device according to claim 1, further comprising at least one mechanical connection element between the eyepiece frame and the first optical element for accommodating the optical unit in the eyepiece frame.

3. The eyepiece device according to claim 2, wherein the mechanical connection element is a bonding bore filled with adhesive.

4. The eyepiece device according to claim 1, wherein the expansion chamber comprises the second optical element having a smaller diameter than the first optical element.

5. The eyepiece device according to claim 1, wherein the first optical element is formed of a first material having a first thermal expansion coefficient and the second material has a second thermal expansion coefficient, wherein the second thermal expansion coefficient is greater than the first thermal expansion coefficient.

6. The eyepiece device according to claim 5, wherein the second thermal expansion coefficient is greater than the first thermal expansion coefficient by at least a factor of two.

7. An eyepiece comprising the eyepiece device according to claim 6, wherein the optical unit comprises an eyepiece lens of the eyepiece.

8. A surgical instrument comprising the eyepiece according to claim 7.

9. The eyepiece device according to claim 1, wherein the first optical element is formed from a first material having a first Abbe number and the second material having a second Abbe number, wherein the second Abbe number is greater than the first Abbe number.

10. The eyepiece device according to claim 1, wherein the second material is an ED glass.

11. The eyepiece device according to claim 10, wherein an Abbe number of the second material is greater than 75.

12. The eyepiece device according to claim 1, wherein the first and second optical elements are lenses and the optical unit is one of an achromat or an apochromat.

* * * * *